United States Patent [19]

Kahler

[11] Patent Number: 4,925,376

[45] Date of Patent: May 15, 1990

[54] PERISTALTIC PUMP WITH TUBE HOLDING MECHANISM

[75] Inventor: William F. Kahler, Johns Island, S.C.

[73] Assignee: Tek-Aids, Inc., Charleston, S.C.

[21] Appl. No.: 217,232

[22] Filed: Jul. 11, 1988

Related U.S. Application Data

[63] Continuation-in-part of Ser. No. 66,759, Jun. 26, 1987, Pat. No. 4,813,855.

[51] Int. Cl.$^5$ .............................................. F04B 43/12
[52] U.S. Cl. ...................................... 417/477; 417/476
[58] Field of Search ............................... 417/474–477; 251/4, 6

[56] References Cited

U.S. PATENT DOCUMENTS

| | | | |
|---|---|---|---|
| 3,137,240 | 6/1964 | Hunt | 417/477 |
| 3,138,104 | 6/1964 | Cantor | 417/477 X |
| 4,187,057 | 2/1980 | Xanthopoulos | 417/477 X |
| 4,210,138 | 7/1980 | Jess et al. | 417/477 X |
| 4,211,519 | 7/1980 | Hogan | 417/477 X |
| 4,519,754 | 5/1985 | Minick | 417/477 |
| 4,552,516 | 11/1985 | Stanley | 417/477 |

Primary Examiner—Leonard E. Smith
Assistant Examiner—Eugene L. Szczecina, Jr.
Attorney, Agent, or Firm—John S. Hale

[57] ABSTRACT

A peristaltic pump for pumping fluids through a flexible tube is described which has a quick release and engagement mechanism that permits easy and rapid removal or insertion of the flexible tube into the device. The quick release and engagement mechanism of the invention consists of a shoe mounted for vertical displacement on the body of the pump. Upward movement of the shoe engages the flexible tube holding the fluid to be pumped and locks the tube against the roller assembly containing an eccentrically mounted roller which intermittently engages the tube and forces fluid out of it. To disengage the flexible tube from the pump, the shoe is moved downward out of contact with the flexible tube.

9 Claims, 2 Drawing Sheets

U.S. Patent May 15, 1990 Sheet 2 of 2 4,925,376
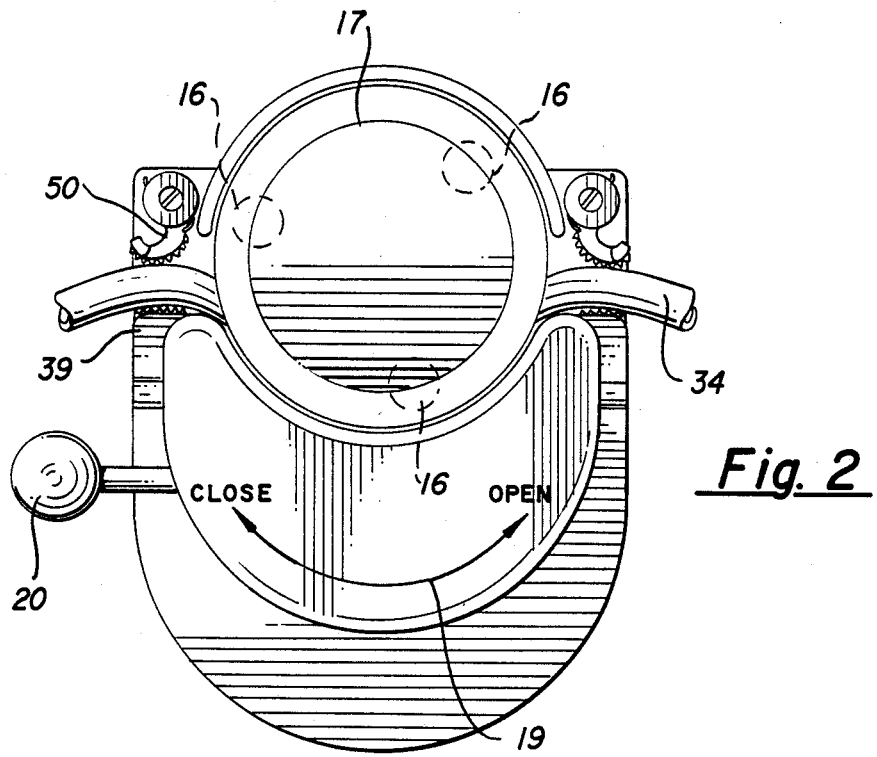
Fig. 2
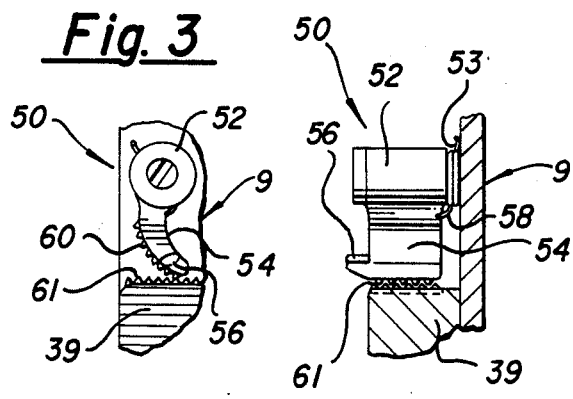
Fig. 3
Fig. 4
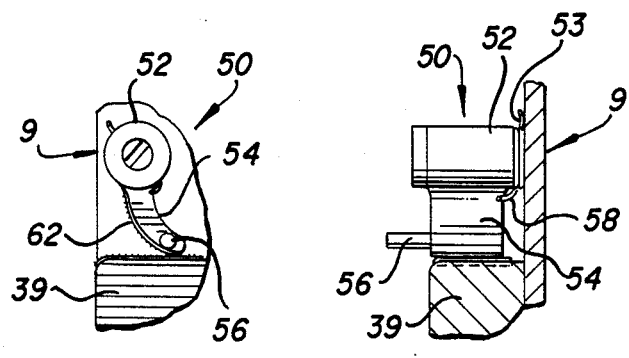
Fig. 5
Fig. 6

PERISTALTIC PUMP WITH TUBE HOLDING MECHANISM

This application is a continuation-in-part of Application Ser. No. 066,759 filed June 26, 1987, now U.S. Pat. No. 4,813,855.

SUMMARY OF THE INVENTION

The present invention is directed to a peristaltic pump for pumping fluids having a unique, quick release mechanism for inserting or removing a flexible tube carrying the liquid which is being pumped. Once the flexible tube is engaged by a closure member, cam assemblies on each side of the closure member hold the tube in place to keep it from walking during the pumping operation. The invention is particularly useful in the medical arts for pumping biological fluids such as urine or therapeutic agents in liquid form.

BACKGROUND OF THE INVENTION

Peristaltic pumps for moving fluids through flexible tubing are known in the art and have found particular application in the medical sciences both for moving biological fluids and for administering therapeutic agents. Typically in such peristaltic pumps, a rotor is mounted eccentrically on a shaft so that rotation of the shaft causes the rotor to transcribe an orbital path in which it is intermittently brought into pressure contact with a flexible length of tubing to compress the tubing and thereby force liquid through the tubing. Pumps of this type are, for example, described in U.S. Pat. No. 4,559,040 to Horres et al. which shows a peristaltic pump having a segmented stator chamber and U.S. Pat. Nos. 4,540,351 and 4,631,007 both to Olson describing peristaltic pumps which are provided with hinged jaws to permit insertion and removal of the flexible tube carrying the liquid being pumped.

As exemplified by the prior art described above, one of the problems encountered with peristaltic pumps is the complexity of the mechanism for holding the flexible tubing in the pump against the rotating pressure member. While it is necessary during the pumping operation for the flexible tubing to be held securely in the pump against a rigid surface so that the orbiting rotor can compress the tubing and move the liquid along within it, it is also desirable to provide a mechanism which permits rapid and easy removal or insertion of the flexible tubing without requiring complex disassembly or reassembly procedures. This is a particularly important and critical feature when the peristaltic pumps are being employed as positive displacement pumps in a medical environment either for transporting or measuring biological fluids or to meter liquid therapeutic agents since the attending physician or his assistants are unlikely to have the time or attention to become involved in extensive manipulative procedures and must depend on metering and volumetric measurements from a positive displacement pump designed for this use.

It is accordingly an object of the present invention to provide a peristaltic pump having a closure mechanism which permits quick and easy insertion and securing of a flexible tube carrying the liquid to be pumped, the closure member being provided with cams to keep the tube from "walking" during the pumping operation. It is a further object of the present invention to provide a peristaltic pump having a release mechanism which permits quick and efficient removal of the flexible tube from the pump without requiring dismantling or disassembly of the pump structure.

BRIEF DESCRIPTION OF THE DRAWINGS

FIG. 2 is a front plan view showing the pump of the invention with a length of flexible tubing inserted and the pump closed and ready for operation;

FIG. 3 is an enlarged isolated side elevational view of the cam mechanism used in the present invention;

FIG. 4 is an enlarged isolated front elevational view of the cam mechanism shown in FIG. 3;

FIG. 5 is an enlarged isolated side elevational view of an alternative embodiment of a cam mechanism used in the present invention; and FIG. 6 is an enlarged isolated front elevational view of the cam mechanism shown in FIG. 4.

DETAILED DESCRIPTION OF THE INVENTION

Figure 1:
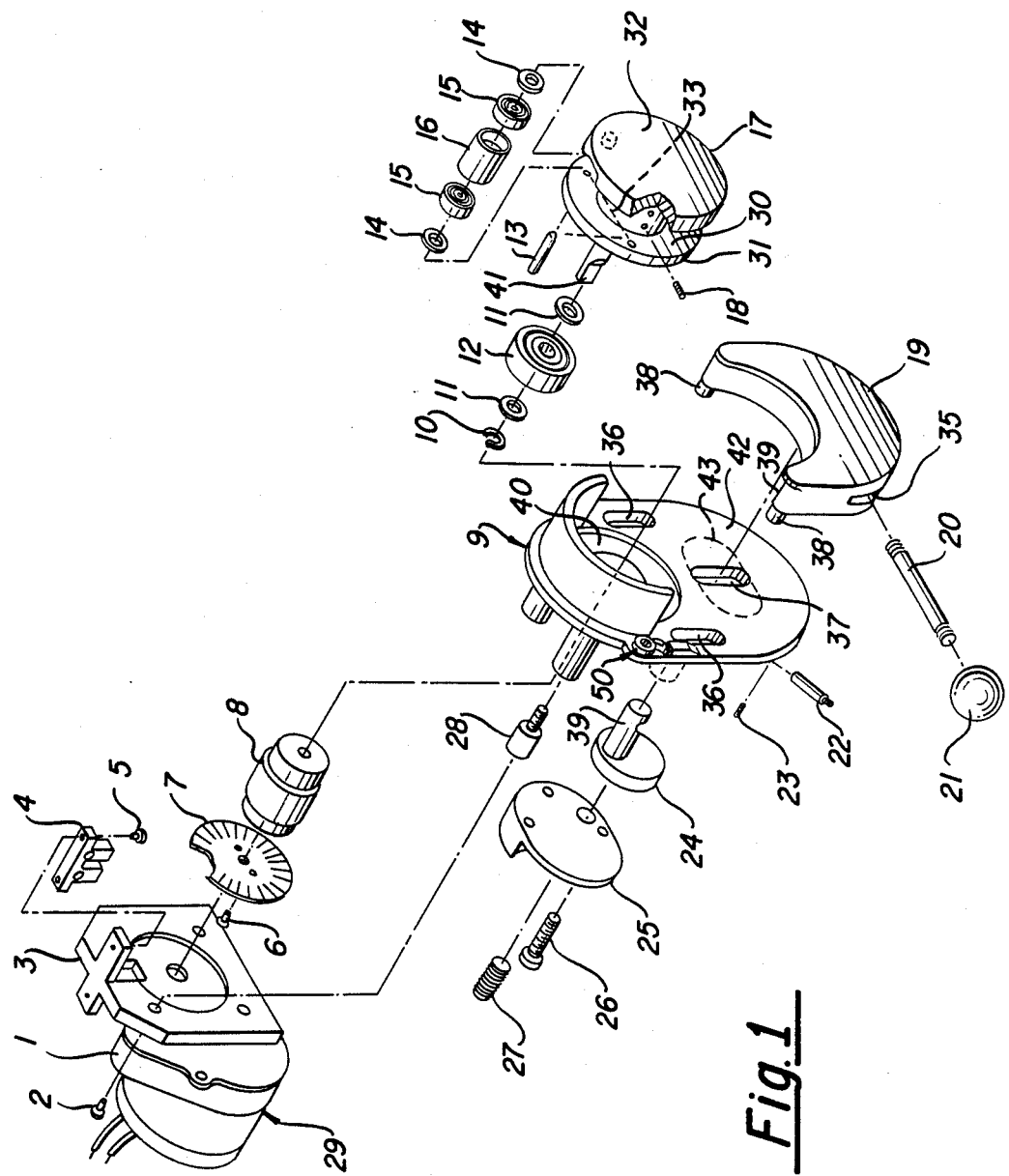
FIG. 1 is an exploded perspective view showing the elements of the present invention.

The preferred embodiment of the invention and best mode is shown in FIGS. 1 through 3 and is directed to a peristaltic pump having a sliding shoe mechanism mounted to the pump housing for quickly and easily permitting the pump to be opened or closed for insertion or removal of the fluid transporting flexible tubing on which the pump acts. More specifically, the present invention consists of a peristaltic pump mechanism having a motor for imparting rotational motion to a roller assembly for engaging and compressing a length of flexible tubing to continuously displace fluid in the tubing. The roller assembly comprises three rollers mounted within a roller housing. The roller housing is disposed on a shaft connected to the motor such that rotation of the shaft causes orbital rotation of the rollers around the shaft. The roller assembly is mounted on a pump housing which is provided with a plurality of slots in which a shoe is slidably mounted below the roller assembly for engaging the flexible tubing. The shoe is adapted for vertical movement relative to the roller housing in order to permit either upward or downward displacement of the shoe to engage and hold a portion of the flexible tubing against cam mechanism mounted on the housing which prevent the tubing from walking through the pump. Vertical movement of the shoe is effected by means of a cam shaft having a cam eccentrically mounted in a cam journal on one end and passing through a vertical slot in the pump housing to engage the shoe on its other end. The cam acts against bearing surfaces of the cam journal formed in the pump housing when the cam shaft is turned to cause vertical movement of the shaft and associated shoe.

The invention will, however, be more fully appreciated by having reference to the accompanying drawings FIGS. 1 through 6, FIGS. 1 through 3 illustrating a best mode and preferred embodiment of the present invention. Directing attention to FIG. 1 of the drawings, a pump housing 9 is shown to which an electric motor 29 and an associated gear mechanism 1 (which is well known in the art) are attached by means of flexible motor mounts 28 and associated mounting screws 2 which isolate both noise and vibration. A circular recessed cavity 40 is defined by the upper portion of pump body 9 to receive a roller housing 17. The roller housing comprises a pair of circular disks or plates 31 and 32 joined together by a shaft 33 of reduced diameter to define an annular slot 30. A roller 16 is mounted eccentrically within the roller housing 17 by means of roller pin 13. Bearings 15 are mounted on pins 13 in the rollers 16 to facilitate revolution of the rollers within the housing and spacers 14 are mounted on pins 13 on each side of rollers 16 to space the rollers 16 in the annular slot 30 of roller housing 17. The roller housing 17 is attached to shaft 41 which passes through bearing 12 mounted in a throughgoing aperture of cavity 40 of the pump body 9. Additional spacers 11 are provided along with clip 10 to maintain the shaft and roller housing properly in alignment with the pump body 9. Rotary motion is imparted to the roller assembly 17 by means of the electric motor 29 to which the shaft 41 is coupled by flexible coupling 8. Mounted between the motor 29 and gear mechanism 1 is a switch and sensor mounting plate 3. The switch and sensor mount 3 holds rotation counting sensor assembly 4 which is attached to the sensor mount 3 by means of screw 5. The rotation counting sensor assembly 4 counts the rotation of the vane 7 which is attached to the coupling 8 by screw 6. The vane 7 is provided with appropriate marking indicia to register on the counting sensor 4 as the coupling and shaft are turned by the motor. The sensor-counter is of conventional design and may sense revolutions of the shaft either mechanically or optically.

Movement of fluid through the flexible tube 34 is imparted by rotation of the roller housing 17 which causes orbital revolution of the rollers 16 with intermittent engagement and compression of the flexible tubing containing the fluid against the shoe 19 and cam mechanisms 50 in its closed position as shown in FIG. 2.

Returning to FIG. 1 of the drawings, it will be seen that the shoe 19 is provided with a concave face which corresponds to the circular configuration of the roller housing 17 when the device is in the closed configuration shown in FIG. 2. The shoe 19 thus comprises a body defining an accurate inner surface which forms a crescent-shaped configuration adapted to engage the flexible tube. The ends of the crescent are provided with a locking surface forming two lock points holding the flexible tube in place preventing the walking of the tube when the roller assembly is rotated. Pump housing 9 is provided with vertical slots 36 in mounting plate 42 to receive the projections 38 on the shoe 19 which permits vertical movement of the shoe 19 against the face of place 42 of the pump housing. This vertical movement of the shoe 19 permits opening and closing to engage the flexible tube with the rollers 16 and roller housing 17 as shown in FIG. 2. Cam shaft 39 passes through the vertical slot 37 plate 42 of the pump housing 9 to engage the shoe 19. A cam 24 is eccentrically mounted on the shaft 39, and the shaft 39 is turned along with the cam 24 by means of lever 20 which passes through a slot 35 in the bottom of the shoe 19 to threadably engage the shaft 39.

Cam cover 25 is mounted on the pump body 9 by means of 3 screws 26. The cam cover 25 retains the cam 24 in the cam journal 43 which extends from the rear of plate 42. Ball plunger set screw 27 is used to lock cam in closed position. The cam journal 43 comprises two bearing surfaces 44 and 45 which in connection with the cam 24 open and close the pump shoe 19. Movement of lever 20 rotates the cam 24 and cam shaft 39 causing vertical displacement of the cam shaft 39 within the slot 37 and corresponding vertical movement of shoe 19 whose projections 38 travel within the slots 36. Thus, by merely rotating the lever arm 20 with knob 21 through the slot 35 from either its position on the left to its position on the right the shoe 19 is caused to slide vertically downward to open the device for insertion or removal of the flexible tubing or slide vertically upward to lock the shoe against the roller housing 17 and associated cam mechanisms 50 with the tubing compressed between the concave inner surface of the shoe 19 and roller 16 within the annular slot 30 of the roller housing and engaged by the knurled surface 60 of the cam mechanism 50 and knurled surface 39 of shoe 19. A safety switch 22 and safety switch set screw 23 are conveniently provided on the pump housing to signal the locking of the cam shaft in place and prevent inadvertent disengagement of the shoe and opening of the pump.

The cam mechanism 50 comprises a cylindrical barrel member 52 rotatably mounted to shaft 53 which is in turn mounted to pump housing 9. The barrel member 52 has an integrally formed curved arm 54 with an outwardly extending projection 56 which serves as a finger hold to lift the cam off of the tubing 34. The underside surface of a curved arm 54 is formed with knurles 60. The knurles grab the tubing and prevent it from walking to the pump as the roller 16 continue to engage the tubing 34. As shown in FIGS. 3 and 4, the top surface 39 of shoe 19 is knurled at 61 so that both the top and bottom surfaces of the tube are held in place when the shoe is closed. A coiled spring number 58 is mounted around shaft 53 and has one end secured to the shaft. The other end of the spring is bent around the end of curved arm 54 and engages the upper surface of arm 54 as is more clearly shown in FIG. 4. An alternate embodiment of the cam is shown in FIGS. 5 and 6 and this embodiment utilizes a similar barrel member 52 rotatably mounted on shaft 53 with a curved arm 54 and spring 58 mounted in the same manner as shown in the previous embodiment disclosed in FIGS. 3 and 4. The alternate embodiment does differ from the preferred embodiment in that the outward projection 56 is cylindrical in shape rather than annular as shown in FIG. 4 and provides a different kind of a finger grasp for release of the curved arm 54. It should be noted that the undersurface of arm 54 is coated with an abrasive material 62 which engages the tubing in a similar manner to that of the knurles 60 grab the tubing and prevent it from walking through the pump. It is also noted that surface 49 of shoe 19 can be coated with a similar abrasive material to provide double grabbing action in much the same manner as the double knurled surfaces 60 and 61 shown in the FIGS. 3 and 4.

In operation, once the flexible tubing 34 containing a fluid to be pumped is inserted between the concave surface of the shoe 19 and the roller housing 17, movement of the lever 20 from the open, right side position to the closed, left side position raises the shoe 19 and brings tubing 34 into pressure contact with rollers 16 between the shoe 19, the knurled surface 49 of shoe 19 and the cam mechanism 50. As housing 17 is turned by the motor, the rollers 16 transcribes an orbital motion which intermittantly brings rollers 16 into pressure contact with the tube 34 to positively displace liquid in the tube through the tube and the cam mechanism keep the tubing from walking through the pump as the tubing 34 is engaged by roller 16.

The present invention, can of course be employed in a number of contexts but finds particular utility with regard to medical practice and the pumping of biological and therapeutic fluids. The present invention is particularly advantageous in its quick and easy manipulation to permit insertion or removal of the flexible tubing which carries the fluids being pumped. As can readily be ascertained from the drawings, the device of the invention can in fact be opened and closed with the use of only a single hand and does not require any disassembly or reassembly procedures.

It will also be apparent that the present invention contemplates various modifications and variations which are considered to fall within the scope of the invention as defined in the claims presented herein.

What is claimed:

1. A peristaltic pump comprising: a housing, means for imparting rotational motion through a shaft to roller assembly means mounted on said housing for engaging and compressing a flexible tube to continuously displace fluid through said flexible tube, said flexible tube being held in contact with said roller assembly means by shoe means moveably mounted on said housing adjacent said roller assembly means and moveable cam means positioned on each side of said roller assembly means, said cam means comprising a shaft, a cam assembly rotatably mounted on said shaft, spring means engaging said cam assembly urging said cam assembly against said flexible tube, a second cam means connected to said shoe means moving said shoe means into a position of engagement with said tubing, said shoe means comprising a body defining an arcuate surface for contacting said flexible tube when moved to a position of engagement, said shoe means being adapted for displacement in one direction to engage a portion of said tube and hold it in engagement with said compressive roller assembly means or displacement in the other direction to disengage said tube from said roller assembly means and permit its removal from said pump.

2. A peristaltic pump comprising: means for imparting rotational motion to a roller assembly for engaging and compressing a flexible tube to cyclically displace fluid in said tube, said roller assembly means comprising roller means mounted within a housing disposed on a shaft connected to said rotational motion means such that rotation of said shaft and housing causes orbital rotation of said roller means around said shaft; said roller assembly means being mounted on a pump housing, shoe means mounted on said pump housing for movement thereon relative to said pump housing to permit either displacement in a first direction to engage and hold a portion of said tube on said roller assembly means together with clamp means for intermittent engagement with said orbiting roller meansor displacement in an opposite direction to the first direction to disengage from said flexible tube on said assembly means and permit removal of said flexible tube from the pump housing, said clamp means comprising a pair of clamp assemblies spaced apart on either side of said roller assembly means adapted to engage and hold a portion of said tube keeping said tube from walking when engaged by said roller assembly means, said shoe means movement being effected by means of a movable shaft which is mounted to said shoe means.

3. The peristaltic pump of claim 2 wherein said clamp means comprises a one piece rotatable cam and shaft, spring means mounted to said shaft engaging said cam to constantly urge said cam toward said tubing.

4. A peristaltic pump as claimed in claim 3 comprising a body, a curved arm extending from said body and a plurality of knurles formed on the surface of said arm.

5. A peristaltic pump as claimed in claim 4 wherein said curved arm has a finger projections member extending outwardly from said arm.

6. A peristatic pum as claimed in claim 4 wherein a surface of said curved arm has an abrasive coating.

7. A peristaltic pump comprising a pump housing, a roller assembly means mounted to said housing, said roller assembly means being adapted to engage and compress a flexible tube to continuously displace measured equal units of fluid passed through said tube, means to drive said roller assembly in a rotational manner, a shoe means moveably mounted on said housing adjacent said roller assembly, means to drive said shoe means in one direction to engage a portion of a flexible tube when said flexible tube is placed in said roller assembly, locking means mounted on said pump housing on either side of said roller assembly means, said shoe means being locked into position against said flexible tube by said drive means and forming a lock when closed, said shoe means comprising a body defining an arcuate inner surface adapted to engage said flexible tube and forming a cresent shaped configuration with the ends of the cresent being provided with a locking surface forming two lock points with said locking means holding said flexible tube in place thereby preventing the walking of the tube when the roller assembly is rotated.

8. A peristaltic pump as claimed in claim 7 wherein the locking surfaces on the ends of the cresent are knurled.

9. A peristaltic pump as claimed in claim 7 wherein the locking surfaces on the ends of the cresent have an abrasive coating.

* * * * *